United States Patent
Ishii et al.

(10) Patent No.: US 6,271,387 B1
(45) Date of Patent: Aug. 7, 2001

(54) PROCESS FOR PRODUCING 1,3-OXAZOLIDINE DERIVATIVES

(75) Inventors: Yasutaka Ishii, Takatsuki; Tatsuya Nakano, Himeji, both of (JP)

(73) Assignee: Daicel Chemical Industries, Ltd., Osaka (JP)

( * ) Notice: Subject to any disclaimer, the term of this patent is extended or adjusted under 35 U.S.C. 154(b) by 0 days.

(21) Appl. No.: 09/492,318

(22) Filed: Jan. 27, 2000

(30) Foreign Application Priority Data

Jan. 26, 1999 (JP) .................................................. 11-016478

(51) Int. Cl.$^7$ ........................ C07D 263/52; C07D 263/04
(52) U.S. Cl. ............................................. 548/216; 548/215
(58) Field of Search ...................................... 548/215, 216

(56) References Cited

FOREIGN PATENT DOCUMENTS 0212742   3/1987 (EP) .

OTHER PUBLICATIONS

Nahar et al. Chemical Abstracts, vol. 108, No. 15, Abstract No. 131640f, XP002137259, p. 740, (Apr. 11, 1988).
Hayashi et al, Chemical Abstracts, vol. 76, No. 9, Abstract No. 46128v, XP002137260, p. 371, (Feb. 28, 1972).
Hamaguchi et al, Agricultural and Biological Chemistry, vol. 49, No. 5, XP002137256, pp. 1509–1511, (May, 1985).
Oda et al, Bulletin of the Chemical Society of Japan, vol. 35, No. 7, XP002137257, pp. 1216–1218, (Jul. 1962).
Bulatova et al, Russian Journal of Organic Chemistry, vol. 30, No. 1, XP002137258, pp. 58–61, (Jun. 10, 1994).

Primary Examiner—Deborah C. Lambkin
Assistant Examiner—Ebenezer Sackey
(74) Attorney, Agent, or Firm—Birch, Stewart, Kolasch & Birch, LLP

(57) ABSTRACT

A process produces 1,3-oxazolidine derivatives by reacting an imine derivative of the following formula (1):

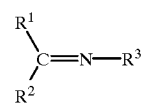

(1)

with an epoxy compound of the following formula (2):

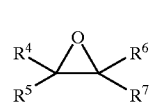

(2)

to yield an oxazolidine derivative of the following formula (3):

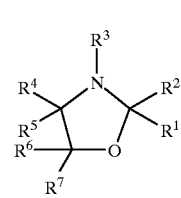

(3)

12 Claims, No Drawings

PROCESS FOR PRODUCING 1,3-OXAZOLIDINE DERIVATIVES

BACKGROUND OF THE INVENTION

1. Field of the Invention

The present invention relates to 1,3-oxazolidine derivatives, which are useful as, for example, pharmaceuticals, agrochemicals, and other fine chemicals or intermediates thereof.

2. Description of the Related Art

As examples of production processes for 1,3-oxazolidine derivatives, a process of reacting a β-aminoalcohol derivative with an aldehyde, and a process of reacting an ethyleneimine derivative with an aldehyde are known. These processes, however, require β-aminoalcohol derivatives or ethyleneimine derivatives as materials which may not be significantly available, and therefore are not always satisfactory for general purpose use and are insufficient in yields.

SUMMARY OF THE INVENTION

Accordingly, it is an object of the present invention to provide a process capable of easily obtaining 1,3-oxazolidine derivatives from readily available materials.

It is another object of the invention to provide a process for producing 1,3-oxazolidine derivatives, which process is satisfactory for general purpose use.

A further object of the invention is to provide a process for obtaining 1,3-oxazolidine derivatives in good yields.

After intensive investigations to achieve the above objects, the present inventors found that a reaction between an imine derivative and an epoxy compound can efficiently yield a corresponding 1,3-oxazolidine derivative. The invention has been accomplished on the basis of the above findings.

Specifically, the invention provides, in an aspect, a process for producing 1,3-oxazolidine derivatives, which process includes the step of reacting an imine derivative of the following formula (1):

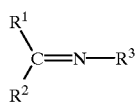

(1)

wherein $R^1$ and $R^2$ are each, identical to or different from each other, a hydrogen atom, a hydrocarbon group or a heterocyclic group, $R^3$ is a hydrogen atom, a hydrocarbon group, a heterocyclic group, a hydroxyl group, a substituted oxy group, or an amino group which may have a substituent, where $R^1$ and $R^2$ may be combined to form a ring with the adjacent carbon atom, with an epoxy compound of the following formula (2):

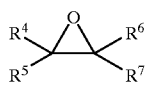

(2)

wherein $R^4$, $R^5$, $R^6$, and $R_7$ are each, identical to or different from one another, a hydrogen atom, a hydrocarbon group or a heterocyclic group, where each combination of $R^4$ and $R^5$, $R^6$ and $R^7$, or $R^4$ and R6 may be combined to form a ring with the adjacent carbon atom or the adjacent carbon-carbon bond, to yield an oxazolidine derivative of the following formula (3):

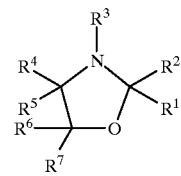

(3)

wherein $R^1$, $R^2$, $R^3$, $R^4$, $R^5$, $R^6$, and $R^7$ have the same meanings as defined above.

The reaction may be performed in the presence of, for example, a compound of a Group 3 element of the Periodic Table of Elements, or another metallic compound catalyst.

The term "imine derivative" as used herein means and includes not only imine compounds in a narrow meaning but also oximes, oxime ethers, hydrazone derivatives, and other various compounds each having a C=N bond.

DESCRIPTION OF THE PREFERRED EMBODIMENT

[Imine Derivative]

In the formula (1), the hydrocarbon group in $R^1$, $R^2$, and R3 includes aliphatic hydrocarbon groups, alicyclic hydrocarbon groups, aromatic hydrocarbon groups, and groups formed from these groups combined together. Such aliphatic hydrocarbon groups include, but are not limited to, methyl, ethyl, propyl, isopropyl, butyl, isobutyl, s-butyl, t-butyl, pentyl, hexyl, decyl, and other alkyl groups each having about 1 to 10 (preferably 1 to 6, and more preferably 1 to 4) carbon atoms; vinyl, allyl, 1-butenyl, and other alkenyl groups each having about 2 to 10 (preferably 2 to 6, and more preferably 2 to 4) carbon atoms; ethynyl, propynyl, and other alkynyl groups each having about 2 to 10 (preferably 2 to 6, and more preferably 2 to 4) carbon atoms.

The alicyclic hydrocarbon groups include, but are not limited to, cyclopropyl, cyclobutyl, cyclopentyl, cyclohexyl, cyclooctyl, and other cycloalkyl groups each having about 3 to 12 (preferably 3 to 8, and more preferably 5 or 6) members; cyclopentenyl, cyclohexenyl, and other cycloalkenyl groups each having about 3 to 12 (preferably 3 to 8, and more preferably 5 or 6) members. Examples of the aromatic hydrocarbon groups are phenyl and naphthyl groups.

Such hydrocarbon groups formed from an aliphatic hydrocarbon group and an alicyclic hydrocarbon group combined together include, but are not limited to, cyclopentylmethyl, cyclohexylmethyl, 2-cyclohexylethyl, and other $C_3$–$C_{12}$ cycloalkyl-$C_1$–$C_4$ alkyl groups, and other cycloalkyl-alkyl groups. Examples of hydrocarbon groups formed from an aliphatic hydrocarbon group and an aromatic hydrocarbon group combined together are $C_7$–$C_4$ aralkyl groups, and other aralkyl groups; and a phenyl group substituted with about one to four $C_1$–$C_4$ alkyl groups, and other alkyl-substituted aryl groups.

Preferred hydrocarbon groups include, for example, $C_1$–$C_{10}$ alkyl groups, $C_2$–$C_{10}$ alkenyl groups, $C_2$–$C_{10}$ alkynyl groups, $C_6$–$C_{10}$ aromatic hydrocarbon groups, $C_3$–$C_{12}$ cycloalkyl-$C_1$–$C_4$ alkyl groups, and $C_7$–$C_{14}$ aralkyl groups.

The hydrocarbon groups may have a variety of substituents, such as a halogen atom, an oxo group, a hydroxyl group, substituted oxy groups (e.g., alkoxy groups, aryloxy groups, aralkyloxy groups, and acyloxy groups), a carboxyl group, substituted oxycarbonyl groups, substituted or unsubstituted carbamoyl groups, a cyano group, a nitro group, substituted or unsubstituted amino groups, and heterocyclic groups.

Heterocyclic rings to constitute the heterocyclic group in $R^1$, $R^2$, and $R^3$ include aromatic heterocyclic rings and non-aromatic heterocyclic rings. Such heterocyclic rings include, but are not limited to, heterocyclic rings each having an oxygen atom as a hetero atom, heterocyclic rings each having a sulfur atom as a hetero atom, and heterocyclic rings each having a nitrogen atom as a hetero atom. Examples of the oxygen-containing heterocyclic rings are furan, tetrahydrofuran, oxazole, isoxazole, and other 5-membered rings; 4-oxo-4H-pyran, tetrahydropyran, morpholine, and other 6-membered rings; and benzofuran, isobenzofuran, 4-oxo-4H-chromene, chroman, isochroman, and other condensed rings. The sulfur-containing heterocyclic rings include, but are not limited to, thiophene, thiazole, isothiazole, thiadiazole, and other 5-membered rings; 4-oxo-4H-thiopyran, and other 6-membered rings; and benzothiophene and other condensed rings. Examples of the nitrogen-containing heterocyclic rings include pyrrole, pyrrolidine, pyrazole, imidazole, triazole, and other 5-membered rings; pyridine, pyridazine, pyrimidine, pyrazine, piperidine, piperazine, and other 6-membered rings; and indole, indoline, quinoline, acridine, naphthyridine, quinazoline, purine, and other condensed rings. The heterocyclic rings may each have a substituent. Such substituents include, for example, those as exemplified in the description of the hydrocarbon groups, alkyl groups (e.g., methyl, ethyl, and other $C_1$–$C_4$ alkyl groups), cycloalkyl groups, and aryl groups (e.g., phenyl and naphthyl groups).

As rings formed by $R^1$ and $R^2$ combined together with the adjacent carbon atom, there may be mentioned cyclobutane, cyclopentane, cyclohexane, cyclohexene, cyclooctane, cyclododecane, and other non-aromatic carbocyclic rings (cycloalkane rings and cycloalkene rings) and non-aromatic heterocyclic rings each having about 3 to 20 (preferably 3 to 15, and more preferably 5 to 12) members. These rings may have any of the aforementioned substituents, and to these rings, another ring (a non-aromatic or aromatic ring) may be condensed.

The substituted oxy groups in $R^3$ include, but are not limited to, methoxy, ethoxy, propoxy, isopropoxy, butoxy, isobutyloxy, and other alkoxy groups (preferably, $C_1$–$C_{10}$ alkoxy groups, and more preferably, $C_1$–$C_6$ alkoxy groups) phenoxy group, and other aryloxy groups; and benzyloxy, 2-phenylethyloxy, and other aralkyloxy groups. Examples of the amino group which may have a substituent in $R^3$ include amino group; methylamino, dimethylamino, ethylamino, diethylamino, propylamino and other mono- or di-alkylamino groups (preferably, mono- or di-$C_1$–$C_6$ alkylamino groups); and 1-pyrrolidinyl, piperidino, morpholino, and other cyclic amino groups.

Preferred examples of $R^1$ and $R^2$ include a hydrogen atom, $C^1$–$C_{10}$ alkyl groups, $C_2$–$C_{10}$ alkenyl groups, $C_2$–$C_{10}$ alkynyl groups, $C_6$–$C_{10}$ aromatic hydrocarbon groups, $C_3$–$C_{12}$ cycloalkyl-$C_1$–$C_4$ alkyl groups, and $C_7$–$C_{14}$ aralkyl groups. Alternately, $R^1$ and $R^2$ may be preferably combined with the adjacent carbon atom to form a non-aromatic carbocyclic ring having about 3 to 15 members. Preferred examples of $R^3$ are $C_1$–$C_{10}$ alkyl groups, $C_2$–$C_{10}$ alkenyl groups, $C_2$–$C_{10}$ alkynyl groups, $C_6$–$C_{10}$ aromatic hydrocarbon groups, $C_3$–$C_{12}$ cycloalkyl-$C_1$–$C_4$ alkyl groups, and $C_7$–$C_{14}$ aralkyl groups.

The imine derivatives of the formula (1) may be either ketimines in which both $R^1$ and $R^2$ are not hydrogen atoms, or aldimines in which at least one of $R^1$ and $R^2$ is a hydrogen atom.

Typical examples of the imine derivatives of the formula (1) include N-ethylidenemethylamine, N-ethylidenebenzylamine, N-ethylidenecyclohexylamine, N-ethylideneaniline, N-isopropylidenebutylamine, N-isopropylidenebenzylamine, N-isopropylidenecyclohexylamine, N-isopropylideneaniline, N-butylidenebutylamine, N-(1-methylbutylidene)butylamine, N-(1-etylpropylidene) butylamine, N-cyclohexylidenebutylamine, N-cyclohexylidenebenzylamine, and N-benzylideneethylamine.

The imine derivatives of the formula (1) can be obtained by the dehydration condensation of corresponding carbonyl compounds ($R^1R^2C=O$) with corresponding amines ($R^3NH_2$), where necessary in the presence of an acid.

[Epoxy Compound]

In the formula (2), the hydrocarbon group and the heterocyclic group in $R^4$, $R^5$, $R^6$, and $R^7$ respectively include those exemplified as the hydrocarbon groups and heterocyclic groups in the substituents $R^1$ and $R^2$. These hydrocarbon groups and heterocyclic groups may have any of the aforementioned substituents. Preferred hydrocarbon groups include $C_1$–$C_{10}$ alkyl groups, $C_2$–$C_{10}$ alkenyl groups, $C_2$–$C_{10}$ alkynyl groups, $C_6$–$C_{10}$ aromatic hydrocarbon groups, $C_3$–$C_{12}$ cycloalkyl-$C_1$–$C_4$ alkyl groups, and $C_7$–$C_{14}$ aralkyl groups, of which $C_1$–$C_6$ alkyl groups, $C_2$–$C_6$ alkenyl groups, $C_2$–$C_6$ alkynyl groups and phenyl group are typically preferred.

The rings formed by a combination of $R^4$ and $R^5$, $R^6$ and $R^7$, or $R^4$ and $R^6$ together with the adjacent carbon atom or carbon-carbon bond include, but are not limited to, cyclopropane, cyclobutane, cyclopentane, cyclopentene, cyclohexane, cyclohexene, cyclooctane, cyclododecane, and other non-aromatic carbocyclic rings (cycloalkane rings and cycloalkene rings) and non-aromatic heterocyclic rings each having about 3 to 20 members. Each of these rings may have any of the aforementioned substituents, and may have another ring (a non-aromatic or aromatic ring) condensed thereto.

Preferred substituents $R^4$, $R^5$, $R^6$, and $R^7$ include a hydrogen atom and the groups exemplified as the preferred hydrocarbon groups.

Typical examples of the epoxy compounds of the formula (2) include, but are not limited to, ethylene oxide, propylene oxide, 1,2-epoxybutane, 1,2-epoxypentane, 1,2-epoxyhexane, 1,2-epoxy-2-methylpropane, 1,2-epoxy-2-methylbutane, 2,3-epoxy-2-methylbutane, 2,3-epoxy-2,3-dimethylbutane, styrene oxide, and α-methylstyrene oxide.

The epoxy compounds of the formula (2) can be obtained by, for example, reacting corresponding olefins ($R^4R^5C=CR^6R^7$) with peracids.

[Reaction]

A reaction in the invented process can proceed even in the absence of a catalyst, but it should be preferably preformed in the presence of a catalyst for improving the reaction rate. Such catalysts include metallic compound catalysts. Examples of the metallic compounds are transition metal compounds (compounds of Groups 3 to 12 elements of the Periodic Table of Elements), compounds of Group 13, 14 and 15 elements of the Periodic Table of Elements. Among these compounds, transition metal compounds are preferred, of which compounds of Group 3 and 4 elements of the Periodic Table of Elements, especially compounds of Group 3 elements of the Periodic Table of Elements, are typically preferred.

The valency of the metal element in the metallic compound is not particularly limited, and is from about 0 to 4, and typically from about 2 to 4 in many cases. Such metallic compounds include, but are not limited to, elementary metals, hydroxides, oxides (including complex oxides), halides (fluorides, chlorides, bromides, and iodides), salts of oxo acids (e.g., nitrates, sulfates, phosphates, borates, and carbonates), oxo acids, isopolyacids or their salts, heteropolyacids or their salts, and other inorganic compounds; salts of organic acids (e.g., salts of, hydrocyanic acid; acetic acid, trichloroacetic acid, trifluoroacetic acid, propionic acid, naphthenic acid, stearic acid, maleic acid, tartaric acid, and other carboxylic acids; methanesulfonic acid, trifluoromethanesulfonic acid, ethanesulfonic acid, benzenesulfonic acid, p-toluenesulfonic acid, and other sulfonic acids), complexes, and other organic compounds.

Such ligands to constitute the complexes include OH (hydroxo), alkoxy (e.g., methoxy, ethoxy, propoxy, and butoxy), acyl (e.g., acetyl, and propionyl), alkoxycarbonyl (e.g., methoxycarbonyl, and ethoxycarbonyl), acetylacetonato, cyclopentadienyl group, $C_1$–$C_4$ alkyl-substituted dicyclopentadienyl groups (e.g., pentamethyldicyclopentadienyl), $C_1$–$C_4$ alkyl groups (e.g., methyl and ethyl groups), halogen atoms (e.g., chlorine, and bromine atoms), CO, CN, oxygen atom, $H_2O$ (aquo), phosphines (triphenylphosphine, and other triarylphosphines), and other phosphorus compounds, $NH_3$ (ammine), NO, $NO_2$ (nitro), $NO_3$ (nitrato), ethylenediamine, diethylenetriamine, pyridine, phenanthroline, and other nitrogen-containing compounds, tetrahydrofuran, and other oxygen-containing compounds.

The compounds of Group 3 and Group 4 elements of the Periodic Table of Elements as the typically preferred metallic compounds will now be described in further detail. The Group 3 elements of the Periodic Table of Elements include rare earth elements [e.g., scandium, yttrium, and lanthanoids elements (lanthanum, cerium, praseodymium, neodymium, promethium, samarium, europium, gadolinium, terbium, dysprosium, holmium, erbium, thulium, ytterbium, and lutetium)], and actinoids elements (e.g., actinium). Preferred Group 3 elements of the Periodic Table of Elements are rare earth elements, and are typically lanthanoids elements, of which samarium is specifically preferred. The Group 4 elements of the Periodic Table of Elements include titanium, zirconium, and hafnium.

By taking samarium compounds as example, concrete examples of the compounds of Group 3 elements of Periodic Table of Elements include samarium(II) hydroxide, samarium(III) hydroxide, samarium(II) oxide, samarium (III) oxide, samarium(II) iodide, samarium(III) iodide, samarium(II) bromide, samarium(III) bromide, samarium (II) chloride, samarium(III) chloride, samarium(II) nitrate, samarium(II) sulfate, samarium(II) phosphate, samarium(II) carbonate, and other inorganic compounds; samarium(II) acetate, samarium(III) acetate, samarium(II) trichloroacetate, samarium(III) trichloroacetate, samarium (II) trifluoroacetate, samarium(III) trifluoroacetate, samarium (II) trifluoromethanesulfonate, samarium(III) trifluoromethanesulfonate, acetylacetonatosamarium(II), acetylacetonatosamarium(III), chlorobis(η-cyclopentadienyl)samarium(III), chlorobis(η-pentamethylcyclopentadienyl) samarium(III)-tetrahydrofuran, dichlorobis(η-pentadienyl)samarium(III)-tetrahydrofuran, lithium tetra(allyl)samarium(III), tetra(t-butyl)lithiumsamarium(III)-tetrahydrofuran, tris(η-cyclopentadienyl)samarium(III), bis(η-pentamethylcyclopentadienyl) samarium(II)-tetrahydrofuran, hydridobis(η-pentamethylcyclopentadienyl)samarium (III), and alkylsamarium(II) iodide. As compounds of the other Group 3 elements of the Periodic Table of Elements, those corresponding to the samarium compounds can be mentioned.

By taking zirconium compounds as example, practical examples of the compounds of Group 4 elements of the Periodic Table of Elements include zirconium(IV) hydroxide, zirconium(IV) oxide, zirconium(IV) iodide, zirconyl(IV) iodide, zirconium(IV) bromide, zirconyl(IV) bromide, zirconium(IV) chloride, zirconyl(IV) chloride, zirconium(IV) nitrate, zirconyl(IV) nitrate, zirconium(IV) sulfate, zirconyl(IV) sulfate, zirconium(IV) phosphate, zirconyl(IV) phosphate, zirconium(IV) carbonate, zirconyl (IV) carbonate, and other inorganic compounds; and zirconium(IV) oxalate, acetylacetonatozirconium(IV), chlorobis(η-cyclopentadienyl)methylzirconium(IV), trichloro(η-cyclopentadienyl)zirconium(IV), trichloro(η-pentamethylcyclopentadienyl)zirconium(IV), bis(η-pentamethylcyclopentadienyl)diiodozirconium(IV), and other organic compounds. As compounds of the other Group 4 elements of the Periodic Table of Elements, those corresponding to the zirconium compounds can be mentioned.

The catalyst can be used either in a homogenous system or in a heterogenous system. The catalyst may be used as being supported by a carrier. As the carrier, activated carbon, silica, alumina, silica-alumina, zeolite, or other porous carriers are used in many cases. The ratio of the catalytic component to the carrier is, for example, about 0.1 to 50 parts by weight, and preferably about 0.5 to 30 parts by weight relative to 100 parts by weight of the carrier.

Each of the above catalysts can be used alone or in combination. The amount of the catalyst can be selected within a wide range, and is, for example, from about 0.00001 to about 1 mole, preferably from about 0.001 to about 0.5 mole, and more preferably from about 0.01 to about 0.25 mole relative to 1 mole of the compound of the formula (1).

The reaction between the imine derivative of the formula (1) and the epoxy compound of the formula (2) is performed in the presence of, or in the absence of, a solvent. Such solvents include, but are not limited to, hexane, octane, and other aliphatic hydrocarbons; cyclohexane and other alicyclic hydrocarbons; benzene, toluene, and other aromatic hydrocarbons; chloroform, dichloromethane, dichloroethane, carbon tetrachloride, chlorobenzene, trifluoromethylbenzene, and other halogenated hydrocarbons; acetone, ethyl methyl ketone, cyclohexanone, and other ketones; diethyl ether, diisopropyl ether, dimethoxyethane, tetrahydrofuran (THF), dioxane, and other ethers; ethyl acetate, butyl acetate, and other esters; acetonitrile, propiononitrile, benzonitrile, and other nitrites; dimethylformamide (DMF), dimethylacetamide, N-methylpyrrolidone, dimethyl sulfoxide, and other non-protic polar solvents; and mixtures of these solvents. Preferred solvents are ethers and non-protic polar solvents, for example.

The proportion of the imine derivative of the formula (1) to the epoxy compound of the formula (2) can be selected within an appropriate range according production costs and reactivity, and either one of the two reactants can be used in an excessive amount relative to the other. For example, the epoxy compound can be used in an amount of about 1.1 to 3 moles relative to 1 mole of the imine compound.

The reaction temperature can be selected within an appropriate range according to, for example, the species of the reactants, and falls in the range from about −20° C. to about +200° C., preferably from about 0° C. to about 150° C., more preferably from about 0° C. to about 100° C., and typically from about 10° C. to 60° C. The reaction time may be selected within an appropriate range of, for example, from about 10 minutes to about 48 hours. The reaction may be performed in a batch system, a semi-batch system or a continuous system.

The reaction between the imine derivative of the formula (1) and the epoxy compound of the formula (2) yields a corresponding adduct, i.e. a 1,3-oxazolidine derivative of the formula (3). The nitrogen atom of the imine derivative may be generally bonded to one carbon atom that exhibits a less steric hindrance of the two carbon atoms constituting the epoxy group of the epoxy compound.

After the completion of the reaction, reaction products can be easily separated and purified in a conventional manner. Such conventional manners include, for example, filtration, concentration, distillation, extraction, crystallization, recrystallization, column chromatography and other separation and purification means, or any combination of these means.

According to the invention, 1,3-oxazolidine derivatives can be easily and efficiently obtained from readily available materials. In addition, a wide variety of 1,3-oxazolidine derivatives can be obtained in good yields and the invented process is satisfactory for general purpose use.

The present invention will now be illustrated in more detail with reference to several inventive examples below, which are not intended limiting the scope of the invention.

EXAMPLE 1

A mixture of 1 mmol of N-isopropylidenebenzylamine, 2 mmol of 1,2-epoxy-2-methylpropane, 0.05 mmol of samarium(II) iodide ($SmI_2$), and 1 ml of tetrahydrofuran was stirred at room temperature for 5 hours. The isolation of products in a reaction mixture by column chromatography revealed that 3-benzyl-2,2,5,5-tetramethyl-1,3-oxazolidine was formed in yield of 98%.

EXAMPLE 2

The procedure of Example 1 was repeated, except that samarium(II) iodide ($SmI_2$) was not used, to yield 3-benzyl-2,2,5,5-tetramethyl-1,3-oxazolidine in yield of 20%.

EXAMPLE 3

A mixture of 1 mmol of N-isopropylidenebutylamine, 2 mmol of 1,2-epoxy-2-methylpropane, 0.05 mmol of samarium(II) iodide ($SmI_2$), and 1 ml of tetrahydrofuran was stirred at room temperature for 5 hours. The isolation of products in a reaction mixture by column chromatography revealed that 3-butyl-2,2,5,5-tetramethyl-1,3-oxazolidine was formed in yield of 92%.

EXAMPLE 4

A mixture of 1 mmol of N-(2-ethylpropylidene)butylamine, 2 mmol of 1,2-epoxy-2-methylpropane, 0.05 mmol of samarium(II) iodide ($SmI_2$), and 1 ml of tetrahydrofuran was stirred at room temperature for 5 hours. The isolation of products in a reaction mixture by column chromatography revealed that 3-butyl-2,2-diethyl-5,5-dimethyl-1,3-oxazolidine was formed in yield of 90%.

EXAMPLE 5

A mixture of 1 mmol of N-cyclohexylidenebutylamine, 2 mmol of 1,2-epoxy-2-methylpropane, 0.05 mmol of samarium(II) iodide ($SmI_2$), and 1 ml of tetrahydrofuran was stirred at room temperature for 5 hours. Products in the reaction mixture was isolated through column chromatography to yield 4-aza-4-butyl-2,2-dimethyl-1-oxaspiro[4.5]decane of the following formula in yield of 85%.

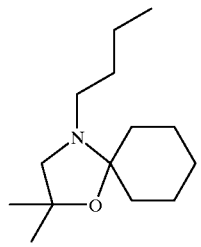

EXAMPLE 6

A mixture of 1 mmol of N-(1-methylbutylidene)butylamine, 2 mmol of 1,2-epoxy-2-methylpropane, 0.05 mmol of samarium(II) iodide ($SmI_2$) and 1 ml of tetrahydrofuran was stirred at room temperature for 5 hours. Column chromatographic isolation of products in a reaction mixture revealed that 3-butyl-2,5,5-trimethyl-2-propyl-1,3-oxazolidine was formed in yield of 59%.

EXAMPLE 7

A mixture of 1 mmol of N-butylidenebutylamine, 2 mmol of 1,2-epoxy-2-methylpropane, 0.05 mmol of $Cp^*_2Sm(THF)_2$, and 1 ml of tetrahydrofuran was stirred at room temperature for 5 hours. Products in a reaction mixture were isolated through column chromatography to yield 3-butyl-5,5-dimethyl-2-propyl-1,3-oxazolidine in yield of 53%.

Other embodiments and variations will be obvious to those skilled in the art, and this invention is not to be limited to the specific matters stated above.

What is claimed is:

1. A process for producing 1,3-oxazolidine derivatives, said process comprising: reacting an imine derivative of the following formula (1):

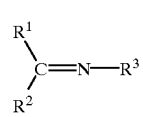

(1)

wherein $R^1$ and $R^2$ are each, identical to or different from each other, a hydrogen atom, a hydrocarbon group or a heterocyclic group, where $R^1$ and $R^2$ are optionally combined to form a ring with the adjacent carbon atom, $R^3$ is a hydrogen atom, a hydrocarbon group, a heterocyclic group, a hydroxyl group, a substituted oxy group, or an amino group which may have a substituent, with an epoxy compound of the following formula (2):

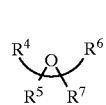

(2)

wherein $R^4$, $R^5$, $R^6$, and $R^7$ are each, identical to or different from one another, a hydrogen atom, a hydrocarbon group or a heterocyclic group, where each combination of $R^4$ and $R^5$, $R^6$ and $R^7$, or $R^4$ and $R^6$ may be combined to form a ring with the adjacent carbon atom or the adjacent carbon-carbon bond, in the presence of a metallic compound catalyst comprising a compound of a Group 3 element of the Periodic Table of Elements to yield an oxazolidine derivative of the following formula (3):

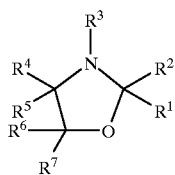

(3)

wherein $R^1$, $R^2$, $R^3$, $R^4$, $R^5$, $R^6$, and $R^7$ have the same meanings as defined above.

2. The process according to claim 1, wherein the reaction is performed in the presence of a compound of the lanthanoid series of elements in Group 3 of the Periodic Table of Elements.

3. The process according to claim 1, wherein the reaction is performed in the presence of a samarium compound.

4. The process according to claim 1, wherein the reaction is performed in the presence of a samarium halide.

5. The process according to claim 1, wherein the reaction is performed in the presence of samarium (II) halide.

6. The process according to claim 1, wherein the reaction is performed at room temperature for about 5 hours.

7. The process according to claim 1, wherein the product 3-benzyl-2,2,5,5-tetramethyl-1,3-oxazolidine is prepared by reaction of N-isopropylidenebenzylamine with 1,2-epoxy-2-methylpropane in the presence of samarium iodide.

8. The process according to claim 1, wherein the product 3-butyl-2,2,5,5-tetramethyl-1,3-oxazolidine is formed by reaction of N-isopropylidenebutylamine with 1,2-epoxy-2-methylpropane in the presence of samarium iodide.

9. The process according to claim 1, wherein N-(2-ethylpropylidene-butyl-amine is reacted with 1,2-epoxy-2-methylpropane in the presence of samarium iodide to form the product 3-butyl-2,2-diethyl-5,5-dimethyl-1,3-oxazolidine.

10. The process according to claim 1, wherein the product 4-aza-4-butyl-2,2-dimethyl-1-oxaspiro(4,5)decane is formed from reaction of N-cyclohexylidenebutylamine with 1,2-epoxy-2-methylpropane in the presence of samarium iodide.

11. The process according to claim 1, wherein the product 3-butyl-2,5,5-trimethyl-2-propyl-1,3-oxazolidine is formed by reaction of N-(1-methylbutylidene)butyl-amine with 1,2-epoxy-2-methylpropane in the presence of samarium iodide.

12. The process according to claim 1, wherein the product 3-butyl-5,5-dimethyl-2-propyl-1,3-oxazolidine is prepared by reaction of N-butylidenebutylamine with 1,2-epoxy-2-methylpropane in the presence of a samarium catalyst.

* * * * *